US00PP10006P

United States Patent [19]

Van Der Made

[11] Patent Number: Plant 10,006

[45] Date of Patent: Aug. 19, 1997

[54] ANTIRRHINUM PLANT NAMED LAWHI

[75] Inventor: Taco Van Der Made, Quedlinburg, Germany

[73] Assignee: Saatzucht Quedlinburg, GmbH, Quedlinburg, Germany

[21] Appl. No.: 662,196

[22] Filed: Jun. 12, 1996

[51] Int. Cl.[6] ..... A01H 5/00

[52] U.S. Cl. ..... Plt./87.9

[58] Field of Search ..... Plt./87.9

*Primary Examiner*—James R. Feyrer

*Attorney, Agent, or Firm*—C. A. Whealy

[57] ABSTRACT

A distinct cultivar of Snapdragon plant named Lawhi, characterized by its ability to be asexually propagated by terminal cuttings; hanging or pendulous plant form that is ideal for hanging basket culture; uniform and freely branching habit; numerous pure white flowers; early flowering; and excellent rooting.

3 Drawing Sheets

The present invention relates to a new and distinct cultivar of Snapdragon plant, botanically known as *Antirrhinum majus*, and hereinafter referred to by the cultivar name Lawhi.

The new Snapdragon is a product of a planned breeding program conducted by the inventor in Quedlinburg, Germany. The objective of the breeding program was to create new Snapdragon cultivars having a hanging growth habit, moderate vigor, desirable flower colors, numerous flowers, and strong rooting habit.

The new Snapdragon originated from a cross made by the inventor of the inventor's proprietary Snapdragon seedling selections. The cultivar Lawhi was discovered and selected by the inventor as a flowering plant within the progeny of this cross in a controlled environment in Quedlinburg, Germany.

Asexual reproduction of the new Snapdragon by terminal cuttings taken at Quedlinburg, Germany, has shown that the unique features of this new Snapdragon are stable and reproduced true to type in successive generations.

The following traits have been repeatedly observed and are determined to be the unique characteristics of Lawhi. These characteristics in combination distinguish Lawhi as a new and distinct cultivar:

1. Can be asexually propagated by terminal cuttings. Most commercially available Snapdragon cultivars are generatively propagated by seeds.
2. Hanging or pendulous plant form that is ideal for hanging basket culture. Maintains uniform habit, does not require growth retardants.
3. Freely branching habit.
4. Numerous pure white flowers.
5. Early flowering.
6. Excellent rooting and easy to propagate.

The new Snapdragon has not been observed under all possible environmental conditions. The phenotype may vary somewhat with variations in environment such as temperature, daylength and light intensity, without, however, any variance in genotype.

Compared to the female parent, plants of the new Snapdragon have larger flowers and differ in flower color. Plants of the male parent are upright whereas plants of the new Snapdragon are hanging or pendulous in growth habit.

The accompanying colored photographs illustrate the overall appearance of the new cultivar, showing the colors as true as it is reasonably possible to obtain in colored reproductions of this type.

The first photograph comprises a side perspective view of a typical flowering hanging basket plant of Lawhi with three plants in the container.

The second photograph comprises a top perspective view of immature (top) and mature (bottom) leaves. The upper (left) and under (right) sides of the leaves are shown. To the right of the leaves, a typical flower is shown.

The third photograph comprises a top perspective view of an intact flower (left) and a flower divided (right) to show the flower throat. The flower and foliage colors in these photographs appear different than the actual colors due to light reflectance.

In the following description, color references are made to The Royal Horitcultural Society Colour Chart except where general terms of ordinary dictionary significance are used. The following observations and measurements describe plants grown in Quedlinburg, Germany, under commercial practice in a glass-covered greenhouse with average night temperatures of 12C. and average day temperatures of 15C.

Botanical classification: *Antirrhinum majus* cultivar Lawhi.

Commercial classification: Hanging basket Snapdragon.

Parentage:

*Male, or pollen, parent.*—Proprietary Snapdragon seedling selection.

*Female, or seed, parent.*—Proprietary Snapdragon seedling selection.

Propagation:

*Type.*—Terminal tip cuttings.

*Time to rooting.*—About 28 days with soil temperatures of 20C.

*Rooting habit.*—Strong rooting habit, cuttings propagate easily, roots fine and freely branching.

Plant description:

*Appearance.*—Herbaceous annual with pendulous habit, suitable for hanging basket containers. Bushy and rounded. Freely branching, plants do not require pinching. Moderate growth rate, maintains uniform habit, does not require growth retardants. From a rooted cutting, eight weeks are required to produce a flowering 9-cm container plant.

*Plant diameter in a hanging basket container.*—From top of plant plane to lower flowers, 40 to 50 cm.

*Stem description.*—Internode length: 1.5 to 2.5 cm. Diameter: 2 to 3 mm. Color: 137B. Texture: Pubescent.

*Foliage description.*—Arrangement: Single. Size: Young foliage: Length: About 2.5 cm. Width: About 1 cm. Mature foliage: Length: About 4 cm. Width: About 2.2 cm. Shape: Elliptic. Leaf apex: Acute. Leaf base: Acute. Margin: Entire. Texture: Pubescent. Color: Young foliage upper surface: 147A. Young foliage under surface: 137C. Fully expanded foliage upper surface: 147A. Fully expanded foliage under surface: 137C. Petiole: Length: About 5 mm. Color: 137A.

Flowering description:

*Appearance.*—Bilabiate flowers arranged in leafy terminal racemes.

*Flowering response.*—Under natural conditions, plants flower continuous from May to November in the Northern Hemisphere. Flowers not persistent. Flowers last up to 10 days on the plants.

*Flower bud.*—Size: Length: 1.5 to 2.5 cm. Diameter: 1 to 1.5 cm. Color: Greenish white.

*Flower size.*—Diameter: 2 to 2.5 cm. Depth (height): 4 to 4.5 cm. Margin: Entire, undulating. Texture: Satiny, smooth and glabrous. Color: Upper lip: 155B. Lower lip: 155B. Lower lip palate: 2A. Inside throat: White. Outside throat: 155B.

*Peduncle.*—Aspect: About 70° to the flowering stem. Length: 3 to 6 mm. Diameter: About 1 mm. Color: 137B.

*Sepals.*—Quantity: 5. Shape: Ovate. Tip: Acute. Margin: Entire. Color: 137B.

*Reproductive organs.*—Androecium: Stamen number: 4. Anther size: 1 to 2 mm. Anther color: 16B. Pollen: 17B. Gynoecium: Pistil number: 1. Style length: About 2 cm. Style color: Greenish white. Stigma color: 144A.

Disease resistance: No known Snapdragon diseases observed to date on plants grown under commercial greenhouse conditions.

Seed production: Seed production has not been observed.

It is claimed:

1. A new and distinct cultivar of Snapdragon plant named Lawhi, as illustrated and described.

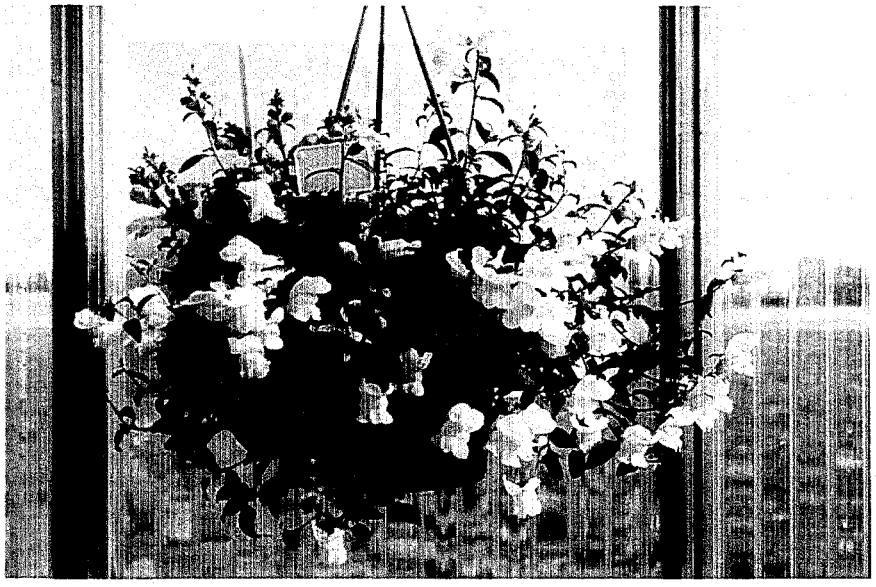

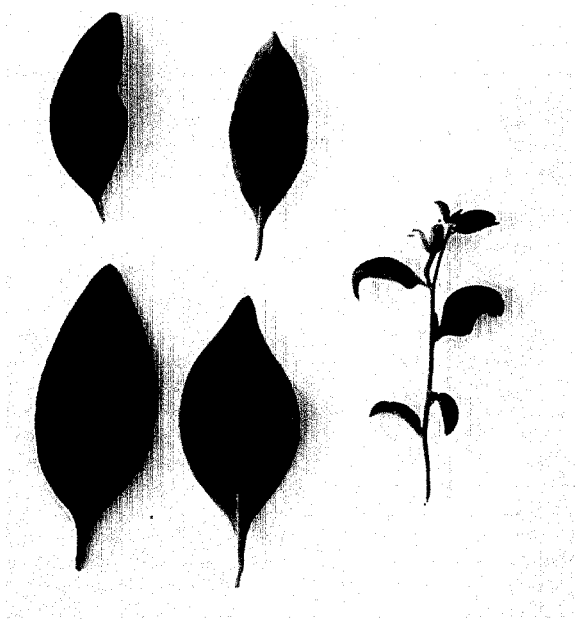

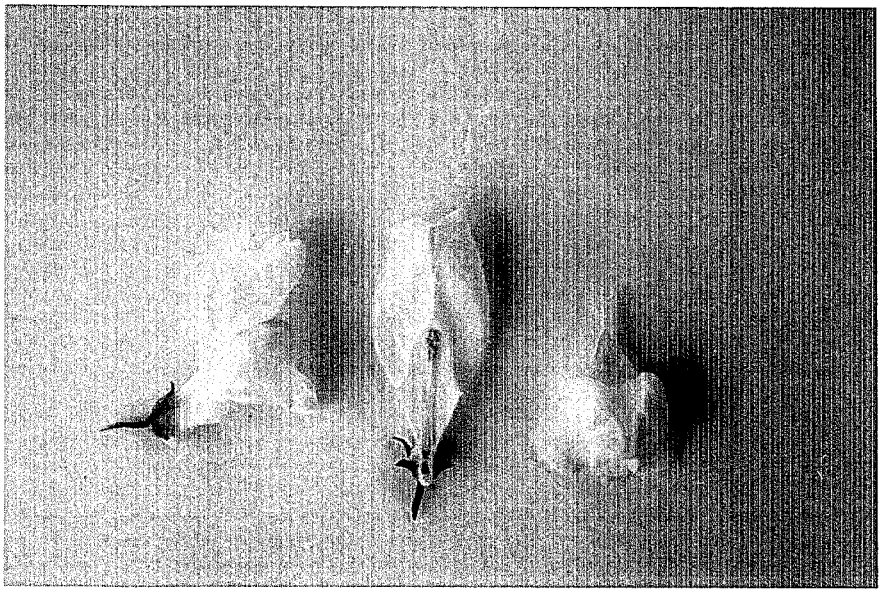

* * * * *